US010258254B2

(12) United States Patent
Furudate

(10) Patent No.: US 10,258,254 B2
(45) Date of Patent: *Apr. 16, 2019

(54) MAGNETIC RESONANCE IMAGING SYSTEM AND MAGNETIC RESONANCE IMAGING METHOD

(71) Applicant: TOSHIBA MEDICAL SYSTEMS CORPORATION, Tochigi-Ken (JP)

(72) Inventor: Naoyuki Furudate, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 399 days.

This patent is subject to a terminal disclaimer.

(21) Appl. No.: 15/252,611

(22) Filed: Aug. 31, 2016

(65) Prior Publication Data

US 2017/0049355 A1    Feb. 23, 2017

Related U.S. Application Data

(62) Division of application No. 11/812,303, filed on Jun. 18, 2007, now Pat. No. 9,462,961.

(30) Foreign Application Priority Data

Jun. 20, 2006 (JP) .................................. 2006-170458
Feb. 9, 2007 (JP) .................................. 2007-030869

(51) Int. Cl.
*A61B 5/055* (2006.01)
*G01R 33/567* (2006.01)
(Continued)

(52) U.S. Cl.
CPC ............ *A61B 5/055* (2013.01); *A61B 5/0037* (2013.01); *A61B 5/0044* (2013.01);
(Continued)

(58) Field of Classification Search
CPC combination set(s) only.
See application file for complete search history.

(56) References Cited

U.S. PATENT DOCUMENTS 3,552,381 A    1/1971   Burns et al.
6,144,201 A   11/2000   Miyazaki
(Continued)

FOREIGN PATENT DOCUMENTS

JP    2000-005144    1/2000
JP    2002-2000054   7/2002
(Continued)

*Primary Examiner* — Serkan Akar
*Assistant Examiner* — Farshad Negarestan
(74) *Attorney, Agent, or Firm* — Nixon & Vanderhye P.C.

(57) ABSTRACT

An MRI prep scan acquires plural sets of echo signals at a plurality of cardiac time phases which are mutually different from each other for each slice and used to generate a plurality of respectively corresponding prep images. Reference information is acquired and displayed for determining a first cardiac time phase and a second cardiac time phase on the basis of the prep images. The first and second cardiac time phases are set in response to an operator's specification. An imaging scan section for acquiring imaging echo signals by performing an imaging scan is performed upon each of the first and second cardiac time phases to acquire imaging echo signals. A first image is generated based on an echo signal of the first cardiac time phase and a second image is generated based on an echo signal of the second cardiac time phase. A differential image is acquired by calculating a difference between the first image and the second image.

21 Claims, 14 Drawing Sheets

(51) Int. Cl.
*G01R 33/563* (2006.01)
*A61B 5/00* (2006.01)
*G01R 33/54* (2006.01)
*G01R 33/561* (2006.01)

(52) U.S. Cl.
CPC ............ *A61B 5/7285* (2013.01); *A61B 5/743* (2013.01); *G01R 33/543* (2013.01); *G01R 33/5635* (2013.01); *G01R 33/5673* (2013.01); *G01R 33/546* (2013.01); *G01R 33/5616* (2013.01); *G01R 33/5617* (2013.01)

(56) References Cited

U.S. PATENT DOCUMENTS

| | | |
|---|---|---|
| 6,708,055 B2 | 3/2004 | Geiser et al. |
| 6,782,286 B2 | 8/2004 | Miyazaki |
| 6,801,800 B2 | 10/2004 | Miyazaki et al. |
| 2003/0016860 A1 | 1/2003 | Sugawara |
| 2003/0042905 A1 | 3/2003 | Miyazaki et al. |
| 2005/0135554 A1 | 6/2005 | Mohr et al. |

FOREIGN PATENT DOCUMENTS

| | | |
|---|---|---|
| JP | 2003-70766 A | 3/2003 |
| JP | 2003-135430 A | 5/2003 |
| JP | 2004-329614 A | 11/2004 |

MAGNETIC RESONANCE IMAGING SYSTEM AND MAGNETIC RESONANCE IMAGING METHOD

CROSS-REFERENCE TO RELATED APPLICATIONS

This application is a divisional of U.S. application Ser. No. 11/812,303 filed Jun. 18, 2007, which claims the benefit of priority from prior Japanese Patent Applications No. 2006-170458, filed Jun. 20, 2006; and No. 2007-030869, filed Feb. 9, 2007, the entire contents of which are incorporated herein by reference.

BACKGROUND OF THE INVENTION

1. Field of the Invention

The present invention relates to a magnetic resonance imaging system and a magnetic resonance imaging method for imaging a subject to be examined by using an electrocardiography-synchronized imaging method (also known as "ECG-gating imaging method") such as an FBI (Fresh Blood Imaging) method, or particularly a Flow-Spoiled FBI method.

2. Description of the Related Art

Examples of an FBI method and a Flow-Spoiled FBI (FS-FBI) method that are one of the angiographic methods used in the magnetic resonance imaging (MRI) are disclosed in Japanese Unexamined Patent Application Publication Nos. 2000-005144 and 2002-200054, respectively.

The FBI method is a non-contrast MRA method capable of virtually displaying images of the blood flow as if a contrast medium were injected. In the FBI method, a subject to be examined (hereinafter, it is simply referred to as a subject) is scanned in synchronization with the cardiac time phase of the subject, the phase being measured on the basis of ECG (electrocardiogram), PPG (photoplethysmogram), or the like, so as to capture high-speed blood flow pumped out from the heart and thus to satisfactorily depict blood vessels. Specifically, in the FBI, a 3-dimensional scanning is performed using different delay times in the diastolic period and the systolic period, the delay time being set between the reception time of an ECG trigger signal (for example, R-wave) and a data acquisition start time, and an arterial blood flow image is generated by differentiating two data components acquired in different periods from each other. As demands arise, a venous blood flow image may be obtained by differentiating the arterial blood flow image from a diastolic image (the arterial and venous blood flow images). The data differentiating process is typically configured to differentiate the blood flow images converted into the actual space from each other, but may be configured such that echo data components are differentiated from each other on a k-space having the same matrix size and the blood flow image is reconstructed on the basis of the differentiated echo data.

However, it may be difficult to distinguish the artery and the vein of the legs from each other in the MRA image captured using the FBI method, since the flow speed in the artery and vein of the legs is relatively low. Accordingly, in the imaging process of the FS-FBI method, a gradient magnetic field having a spoiler pulse (flow spoiled pulse) appended thereto is used in the systolic period. In this way, an arterial signal is suppressed in the systolic period, and the artery and the vein can be distinguished. The spoiler pulse is typically appended to the front and rear ends of a readout gradient magnetic field waveform, but may be appended to a phase encoded gradient magnetic field waveform. The arterial signal can be further suppressed by a flow-dephasing effect when a readout and encoding direction is set in a blood vessel running direction, but the readout and encoding direction may be set in other directions. The important thing is that when a phase encoding direction is set in the same direction as the blood flowing direction (blood vessel running direction), artifacts may be superimposed on the blood vessel and it is thus difficult to extract flow-voids. However, when the phase encoding direction is set in a direction different from the blood flowing direction, it is possible to attain the arterial signal suppressing effect. These imaging methods have a delay time as a parameter of imaging condition. The delay time is set by an operator. Specifically, by comparing images captured by an ECG-prep scan at a plurality of time phases, the operator calculates a time difference between the time phase at which the best image was obtained and a reference time phase (for example, the time phase at which R-wave is generated) and sets the time difference as the delay time. The ECG-prep scan is a preparation scan that executes a preparatory pulse sequence to determine synchronization timings. Additionally, in the ECG-prep scan, the subject is imaged at each of a plurality of time phases with different delay times from the reference time phase of the ECG signal.

According to the known techniques described above, the operator has to determine a proper delay time on the basis of the image obtained by the ECG-prep scan, which imposes a large burden on the operator and makes it difficult to say that the proper delay time determined by the operator is always suitable for the imaging condition.

BRIEF SUMMARY OF THE INVENTION

It is therefore desirable to set the delay time in an easy and precise manner.

According to a first aspect of the invention, there is provided a magnetic resonance imaging system which includes a prep scan section for performing a prep scan acquiring plural sets of echo signals at a plurality of cardiac time phases which are mutually different from each other for each slice; a prep image generating section for generating a plurality of prep images corresponding to the plurality of cardiac time phases on the basis of the plural sets of echo signals, respectively; a reference information acquiring section for acquiring reference information for determining a first cardiac time phase and a second cardiac time phase on the basis of the plurality of prep images; a reference information display section for displaying the reference information; a cardiac time phase setting section for setting the first cardiac time phase and the second cardiac time phase in response to an operator's specification; an imaging scan section for acquiring imaging echo signals by performing an imaging scan upon each of the first cardiac time phase and the second cardiac time phase which are set by the cardiac time phase setting section; and an imaging image generating section for generating a first image based on an echo signal of the first cardiac time phase obtained by the imaging scan section, generating a second image based on an echo signal of the second cardiac time phase obtained by the imaging scan section, and acquiring a differential image by calculating a difference between the first image and the second image.

According to a second aspect of the invention, there is provided a magnetic resonance imaging system which includes a prep scan section for performing a prep scan acquiring plural sets of echo signals at a plurality of cardiac time phases which are mutually different from each other for each slice; a prep image generating section for generating a plurality of prep images corresponding to the plurality of cardiac time phases on the basis of the plural sets of echo signals, respectively; a cardiac time phase determining section for determining a first cardiac time phase and a second cardiac time phase on the basis of the plurality of prep images; an imaging scan section for acquiring imaging echo signals by performing an imaging scan upon each of the first cardiac time phase and the second cardiac time phase which are set by the cardiac time phase determining section; and an imaging image generating section for generating a first image based on an echo signal of the first cardiac time phase obtained by the imaging scan section, generating a second image based on an echo signal of the second cardiac time phase obtained by the imaging scan section, and acquiring a differential image by calculating a difference between the first image and the second image.

According to a third aspect of the invention, there is provided a magnetic resonance imaging method which includes steps of: performing a prep scan acquiring plural sets of echo signals at a plurality of cardiac time phases which are mutually different from each other for each slice; generating a plurality of prep images corresponding to the plurality of cardiac time phases on the basis of the plural sets of echo signals, respectively; acquiring reference information for determining a first cardiac time phase and a second cardiac time phase on the basis of the plurality of prep images; displaying the reference information; setting the first cardiac time phase and the second cardiac time phase in response to an operator's specification; acquiring imaging echo signals by performing an imaging scan upon each of the first cardiac time phase and the second cardiac time phase which are set in the cardiac time phase setting; and generating a first image based on an echo signal of the first cardiac time phase obtained by the imaging scan section, generating a second image based on an echo signal of the second cardiac time phase obtained in the imaging scanning, and acquiring a differential image by calculating a difference between the first image and the second image.

According to a fourth aspect of the invention, there is provided a magnetic resonance imaging method which includes steps of: performing a prep scan acquiring plural sets of echo signals at a plurality of cardiac time phases which are mutually different from each other for each slice; generating a plurality of prep images corresponding to the plurality of cardiac time phases on the basis of the plural sets of echo signals, respectively; determining a first cardiac time phase and a second cardiac time phase on the basis of the plurality of prep images; acquiring imaging echo signals by performing an imaging scan upon each of the first cardiac time phase and the second cardiac time phase which are set in the cardiac time phase determination; and generating a first image based on an echo signal of the first cardiac time phase obtained by the imaging scan section, generating a second image based on an echo signal of the second cardiac time phase obtained in the imaging scanning, and acquiring a differential image by calculating a difference between the first image and the second image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the invention will be described with reference to drawings.

First Embodiment

Figure 1:
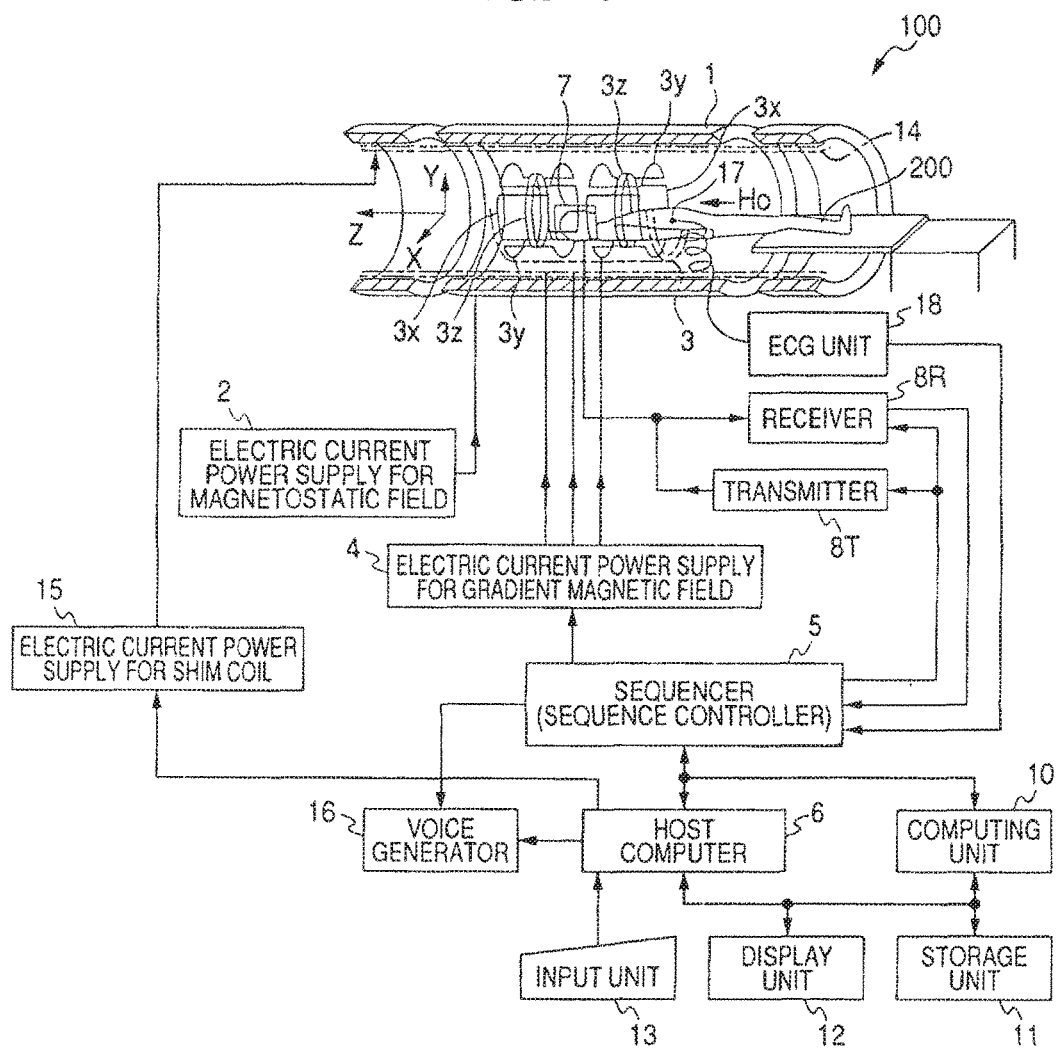
FIG. 1 is a schematic view illustrating a configuration of a magnetic resonance imaging system (MRI system) according to a first embodiment of the invention.

FIG. 1 is a schematic view illustrating a configuration of a magnetic resonance imaging system (MRI system) 100 according to a first embodiment.

The MRI system 100 includes a couch section on which a subject 200 lies down, a magnetostatic field generating section for generating a magnetostatic field, a gradient magnetic field generating section for appending positional information to the magnetostatic field, a transmitting/receiving section for transmitting and receiving a high frequency signal, and a control and operation section responsible for both control of the whole system and image reconstruction. Additionally, the MRI system 100 includes, as components of the sections, a magnet 1, a magnetostatic field power supply 2, a gradient magnetic field coil unit 3, a gradient magnetic field power supply 4, a sequencer (sequence controller) 5, a host computer 6, an RF coil 7, a transmitter 8T, a receiver 8R, an operation unit 10, a storage unit 11, a display unit 12, an input unit 13, a shim coil 14, a shim coil power supply 15 and voice generator 16. In addition, the MRI system 100 is connected to an electrocardiograph section for measuring an ECG signal being employed as a signal indicative of cardiac time phases of the subject 200.

The magnetostatic field generating section includes the magnet 1 and the magnetostatic field power supply 2. For example, a superconductor magnet or a normal conductor magnet can be used as the magnet 1. The magnetostatic field power supply 2 supplies electric current to the magnet 1. With such a configuration, the magnetostatic field generating section generates the magnetostatic field H0 in an axial direction (Z-axis direction) of a cylindrical bore (diagnostic space) into which the subject 200 is inserted. The magnetostatic field generating section includes shim coils 14. The shim coils 14 are supplied with a current from the shim coil power supply 15 under the control of the host computer 6 and generate an offset magnetic field for homogenizing a magnetostatic field.

The couch top of the couch section on which the subject 200 lies down can be inserted into the diagnostic space so that the couch top can be withdrawn.

The gradient magnetic field generating section includes the gradient magnetic field coil unit 3 and the gradient magnetic field power supply 4. The gradient magnetic field coil unit 3 is incorporated in the magnet 1. The gradient magnetic field coil unit 3 includes three pairs of coils 3x, 3y, and 3z used to generate gradient magnetic fields changing in strength in X-axis, Y-axis, and Z-axis directions that are mutually orthogonal. The gradient magnetic field power supply 4 supplies pulsated currents used to generate gradient magnetic fields to the coils 3x, 3y, and 3z under the control of a sequencer 5. In the gradient magnetic field generating section, the pulsated currents supplied from the gradient magnetic field power supply 4 to the coils 3x, 3y, and 3z are controlled, whereby gradient magnetic fields changing in the three X-, Y-, and Z-directions (physical axis directions) are synthesized. Thus, a slice-directional gradient magnetic field GS, a phase-encoding directional gradient magnetic field GE, and a read out directional (frequency-encoding-directional) gradient magnetic field GR, which are mutually orthogonal, can be specified and changed arbitrarily about each of their logic axis directions. The gradient magnetic fields to be applied in the slice direction, the phase encoding direction, and the readout direction are superposed on the static magnetic field H0.

The transmitting/receiving section includes the RF coil 7, the transmitter 8T, and the receiver 8R. The RF coil 7 is located in the vicinity of a subject 200 in the diagnostic space inside the magnet 1. The transmitter 8T and a receiver 8R are connected to the coil 7. The transmitter 8T and the receiver 8R operate under the control of a sequencer 5. The transmitter 8T supplies to the RF coil 7 RF current pulses of the Larmor frequency, which are used to excite the nuclear magnetic resonance (NMR). The receiver 8R receives MR signals (high frequency signals) such as echo signals received by the RF coil 7, carries out various kinds of signal processing, such as pre-amplification, intermediate-frequency conversion, phase detection, low-frequency amplification, and filtering, and A/D-converts them into digital data (raw data) of the MR signals. Furthermore, the control and operation section includes the sequencer 5, the host computer 6, the operation unit 10, the storage unit 11, the display unit 12, the input unit 13 and the voice generator 16.

The host computer 6 has various control functions realized when a predetermined software procedure is executed. One example of the control functions is a function of providing pulse sequence information to the sequencer and managing the entire operations of the system. Another example of the control functions is a function of controlling the respective sections mentioned above so as to perform a MR scan based on the Flow-Spoiled FBI method. A still another example of the control functions is a function of automatically determining a delay time $T_{DL1}$ and $T_{DL2}$ which is a parameter of an imaging condition in the MR scan based on the Flow-Spoiled FBI method.

The sequencer 5 has a CPU and memories. The sequencer 5 stores pulse-sequence information sent from the host computer 6. The CPU of sequencer 5 controls the operations of the gradient magnetic field power supply 4, transmitter 8T, and receiver 8R according to the stored information, and temporarily receives raw data corresponding to MR signals outputted from the receiver 8R so as to transmit them to the operation unit 10. The pulse-sequence information includes all the information required for operating the gradient magnetic field power supply 4, transmitter 8T, and 10 receiver 8R according to a series of pulse sequences. For example, such information includes information about the strength, duration, and application timing of pulsed currents applied to the coils 3x, 3y, and 3z.

As to the pulse sequences, provided that a Fourier transform method is adopted, a two-dimensional (2D) scan or a three-dimensional (3D) scan can be used. As examples of pulse trains available to those scans, preferable are pulse trains on a fast SE (Spin Echo) method, FSE (Fast Spin Echo) method, EPI (Echo Planar Imaging) method, EASE (Fast asymmetric SE) method, or others.

The operation unit 10 receives the raw data sent from the receiver 8R via the sequencer 5. The operation unit 10 maps the raw data in a Fourier space (also known as a k-space or frequency space) formed in its incorporated memory, and performs for each set of data a two-dimensional or three-dimensional Fourier transform with the mapped raw data so as to reconstruct an image in the real space. Moreover, the operation unit 10 is able to perform synthesizing processing and difference-calculation processing (including weighted difference processing) with data of images, if necessary. The synthesizing processing includes an addition processing for every corresponding pixel, a maximum intensity projection (MIP) processing, or the like. As another example of the above synthesizing processing, available is a method by which raw data of a plurality of frames are synthesized into a frame of raw data, as they are, with the axes of the frames matched in the Fourier space. Additionally, the addition processing includes simple addition, averaging, or weighted addition.

The storage unit 11 can preserve image data produced by the above synthesis processing or difference processing as well as reconstructed image data.

The display unit 12 presents various images to users under the control of the host computer 6.

The input unit 13 allows operators to input various information sources desired by the operators such as parameter information for selecting synchronization timing, scan conditions, a pulse sequence, or information about image synthesis processing and difference calculation processing. The input unit 13 sends the inputted information to the host computer 6.

The voice generator 16 outputs, for example, voice messages informing a subject of the start and end of breath hold in response to instructions sent from the host computer 6.

The electrocardiograph section includes an ECG sensor 17 and an ECG unit 18. The ECG sensor 17 is attached to the body of the subject 200 so as to detect an electric ECG signal hereinafter, it is referred to as a sensor signal) of the subject 200. The ECG unit 18 performs various processes including digitization with the sensor signal and sends it to both the host computer 6 and the sequencer 5. A vectorcardiograph can be used as the electrocardiograph section, for example. The sequencer 5 to perform each of an ECG-prep scan and an ECG-gating imaging scan uses this sensor signal measured by the electrocardiograph section, whenever necessary. This enables appropriate setting of synchronous timing on the ECG gating method, and data acquisition can be done by the ECG-gating imaging scan on the set synchronous timing.

Next, an operation of the MRI system 100 configured as mentioned above will be described.

The MRI system 100 can perform the MR scan based on the Flow-Spoiled FBI method. As to the operation for performing this MR scan, for example, the operation disclosed in Japanese Unexamined Patent Application Publication No. 2002-200054 can be available. However, the host computer 6 performs the processing to be described below ahead of the MR scan in order to determine the delay times $T_{DL1}$ and $T_{DL2}$.

Figure 2:
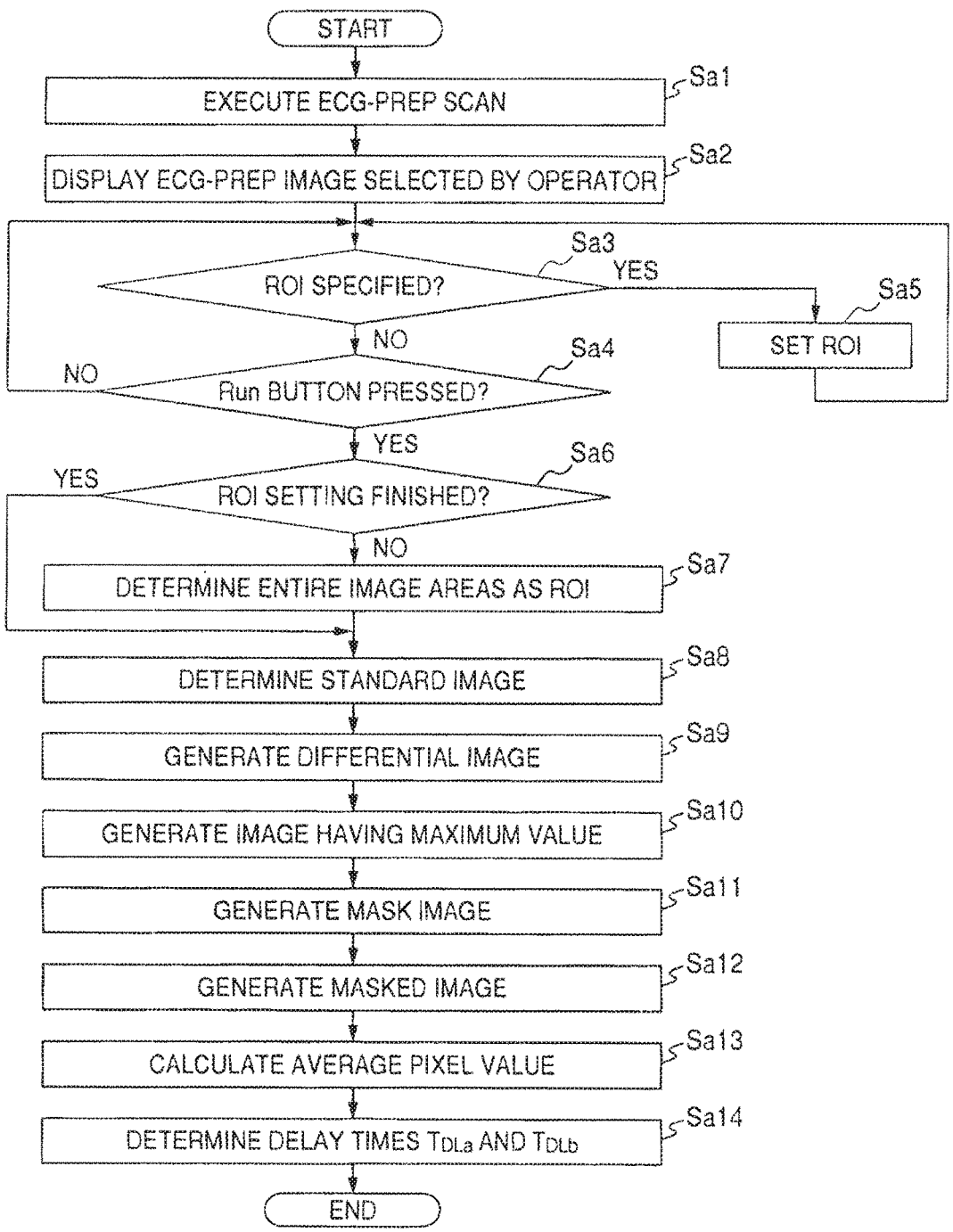
FIG. 2 is a flowchart illustrating the procedures of a host computer shown in FIG. 1 for determining two delay times.

FIG. 2 is a flowchart illustrating the procedures of the host computer 6 for determining the delay times $T_{DL1}$ and $T_{DL2}$.

In the step Sa1, the host computer 6 instructs the sequencer 5 to execute the ECG-prep scan. Then, according to the instructions, the sequencer 5 executes the ECG-prep scan in accordance with the procedures disclosed in Japanese Unexamined Patent Application Publication No. 2002-200054. By using this ECG-prep scan, a plurality of images (hereinafter, referred to as an ECG-prep image) corresponding to mutually different time phases can be obtained. For example, it is possible to obtain ten ECG-prep images corresponding to ten time phases having delay times in the range of 0 to 900 msec from the reference time phase at intervals of 100 msec.

In the step Sa2, the host computer 6 causes the display unit 12 to display ECG-prep image selected by an operator from the plurality of ECG-prep image obtained by the aforementioned ECG-prep scan. Additionally, the host computer 6 causes the GUI (graphical user interface) illustrated in FIG. 3 to be displayed on the screen for displaying the selected ECG-prep image.

Figure 3:
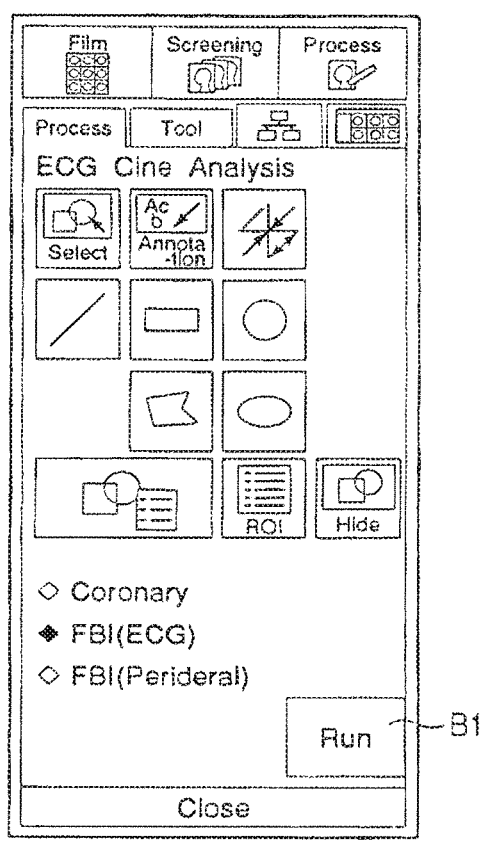
FIG. 3 is a diagram illustrating an example of a GUI displayed with ECG-prep images in accordance with the first embodiment.

In the steps Sa3 and Sa4, the host computer 6 waits until an operation of specifying ROI (region of interest) is performed or a Run button B1 provided on the GUI illustrated in FIG. 3 is pressed.

Figure 4:
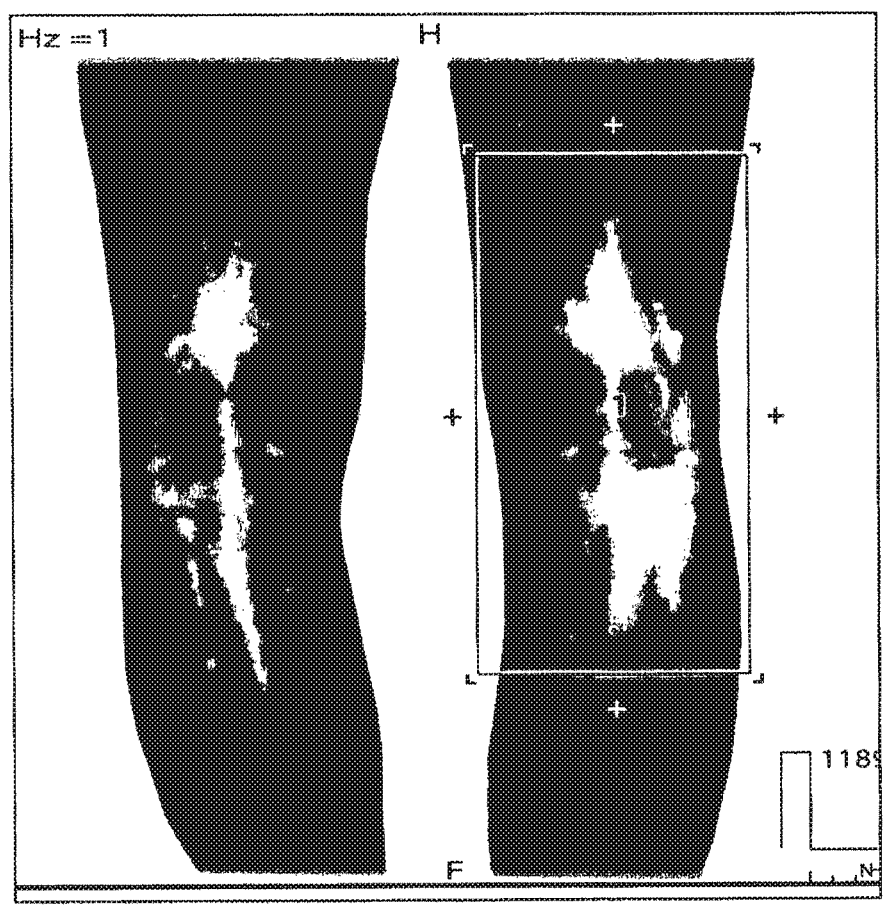
FIG. 4 is a diagram illustrating a setting example of one ROI.
Figure 5:
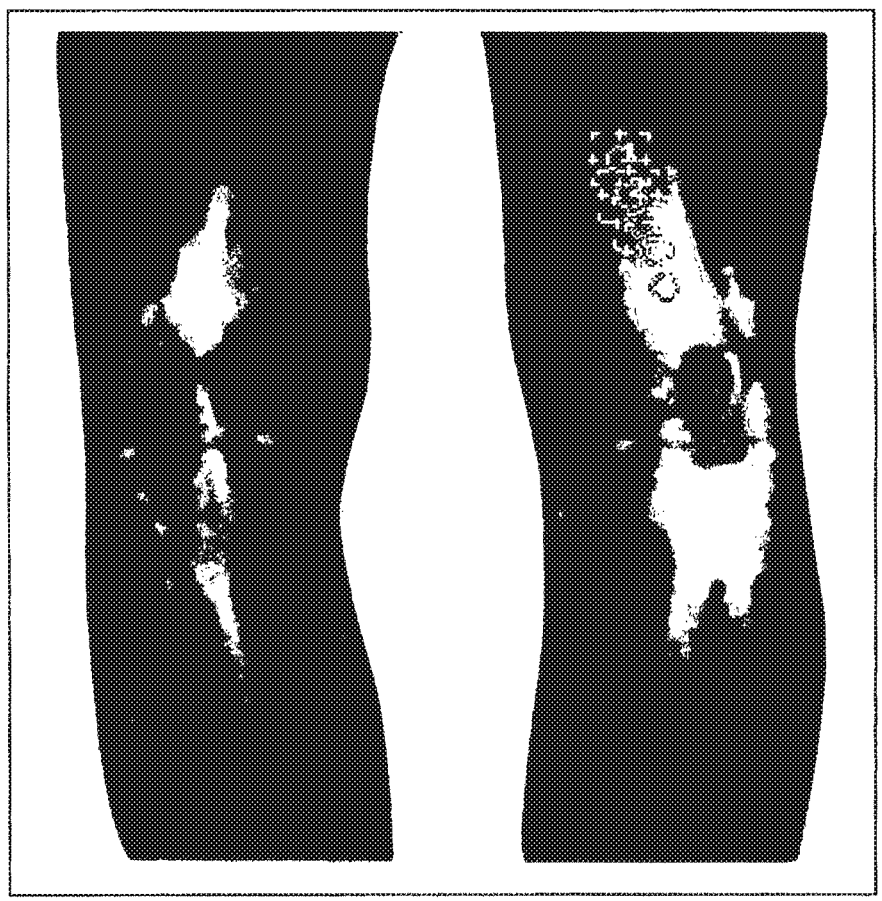
FIG. 5 is a diagram illustrating a setting example of a plurality of ROIs.

Here, in the case where an operator executes the operation of specifying the ROI by using the input unit 13, the operation proceeds from the step Sa3 to the step Sa5, in which in the step Sa5, the host computer 6 sets the ROI depending on the manipulation of the operator. FIG. 4 is a diagram illustrating a setting example of the ROI. When a setting of the one ROI is finished, the host computer 6 returns to the waiting state of the steps Sa3 and Sa4. The host computer 6 sets the plurality of ROIs by repeating the step Sa5 when the operator repeats the manipulation of specifying ROI. FIG. 5 is a diagram illustrating a setting example of a plurality of ROIs. In the FIG. 5, 20 five circular ROIs are set.

Meanwhile, if the Run button B1 is pressed, the operation proceeds from the step Sa4 to the step Sa6, in which in the step Sa6, the host computer 6 judges whether the setting of ROI is finished or not. When the setting of ROI does not exist, the host computer 6 performs the step Sa7 after the step Sa6. In the step Sa7, the host computer 6 sets the entire areas of the ECG-prep image to ROI. Then, the host computer 6 performs the step Sa8. When only one ROI setting exists, the host computer 6 performs the operation of the step Sa8 after the step Sa6 while bypassing the step Sa7.

In the step Sa8, the host computer 6 sets one of the ECG-prep images to the standard image. Specifically, the host computer 6 sets to the standard image the ECG-prep image corresponding to the latest time phase of the time phases having shorter delay time than predetermined time. For example, when the predetermined time is 250 msec, the ECG-prep image corresponding to the time phase of which the delay time is 200 msec is set to the standard image.

By the way, when an operator sets the delay time, the ECG-prep image corresponding to the time phase closest to the systolic period is generally used as the standard image. However, the standard image used in the first embodiment needs not be the ECG-prep image corresponding to the time phase closest to the systolic period. For this reason, the predetermined time mentioned above needs not be set for every imaging process, but can be set to a fixed value. By setting the predetermined time to the fixed value, the standard image can be automatically determined, and thus it is possible to reduce the burden imposed on the operator. The predetermined time is a default value, which may be set in the process of production of the MRI system 100 and may be set arbitrarily by an operator. Additionally, the predetermined time can be specified by an operator whenever the imaging process is performed. Alternately, the predetermined time may be set to an initial value. When the initial value is changed and specified by an operator, the specified value may be used as the predetermined time. When the initial value is not changed and specified by the operator, the initial value may be used as the predetermined time.

In the step Sa9, the host computer 6 generates differential images between the standard image and the respective ECG-prep images other than the standard image. When the ten ECG-prep images mentioned above and an ECG-prep image corresponding to the time phase of which the delay time is 200 msec is set to a standard image, by respectively calculating the differences between the ECG-prep image corresponding to the time phase of which the delay time is 200 msec and the ECG-prep images corresponding to the time phases of which the delay times are 0 msec, 100 msec, and 300 to 900 msec, nine differential images are generated. The host computer 6 generates the differential images corresponding to only ROIs. The differential images become the image having the pixel value based on variation of blood flow relative to the standard image.

In the step Sa10, all differential images generated from the step Sa9 are processed by a maximum-value projection, whereby the host computer 6 generates one of the maximum-value images. The maximum-value image is an image of collecting only the image having the largest variation in blood flow from the differential images.

In the step Sa11, the host computer 6 converts the maximum-value image into a binary image, thereby generating a mask image. The host computer 6 may use the predetermined value which is a threshold for the binary conversion described above, and may use a value calculated by multiplying a factor by size of the maximum signal of the maximum-value image. The factor is less than 1. With respect to the factor, the predetermined value can be used, and the value specified by an operator can be used. Alternately, for example, assuming that an initial value is set to 0.7, when the initial value is changed and specified by an operator, the specified value may be used as the factor, and when the initial value is not changed and specified by an operator, the initial value may be used as the factor. The mask image is defined as an image formed in a way that the pixel value of pixels having a signal intensity not less than the threshold of the maximum-value image is set to 1 and the pixel value of the other pixels is set to 0. That is, the mask image is an image obtained by extracting blood vessel features in a way that the pixel value corresponding to the parts which are more likely to be blood vessels is set to 1, and the pixel value corresponding to the parts which are less likely to be blood vessels is set to 0.

In the step Sa12, the host computer 6 multiplies the mask image and the respective images in the ROIs of all ECG-prep images for every pixel, thereby generating a plurality of masked images. When the ten ECG-prep images mentioned above, ten masked images are generated. The masked image is an image obtained by extracting the parts which are more likely to be blood vessels from the images in the ROIs of the ECG-prep images.

In the step Sa13, the host computer 6 calculates average pixel values with respect to the all pixels in the masked image for every masked image. With such a configuration, each average value is calculated from each time phase of the plurality of ECG-prep image which is the basis of the masked images. When the ten ECG-prep images mentioned above, total ten average values corresponding to the respective ten time phase is obtained.

In the step Sa14, the host computer 6 determines the delay times $T_{DLa}$ and $T_{DLb}$ on the basis of the plurality of average values described above. In detail, the host computer 6 determines that the delay time elapsed from the reference time phase of the time phase corresponding to the minimum value of the plurality of average values obtained in the step Sa13 is the delay time $T_{DLb}$. Additionally, the host computer 6 determines that the delay time elapsed from the reference time phase of the time phase corresponding to the maximum value of the average values obtained in the step Sa13 is the delay time $T_{DLa}$. The blood flow generally becomes the maximum after becoming the minimum. For this reason, a retrieval of the maximum value described above may be performed with respect to only the average values based on the later time phase than the time phase corresponding to the minimum value described above.

When setting the plurality of ROIs, plurality sets of average values corresponding to the respective ROIs are obtained. In this case, the maximum value and minimum value of the sets in which the difference between the minimum value and the maximum value of average values becomes maximum are used for determining the delay times $T_{DLa}$ and $T_{DLb}$.

The delay times $T_{DLa}$ and $T_{DLb}$ (corresponding respectively to minimum and maximum image pixel values) determined in such a way may be used as the delay times $T_{DL1}$ and $T_{DL2}$ to be used for a diagnostic MR scan in accordance with the Flow-Spoiled FBI method disclosed in the Japanese Unexamined Patent Application Publication No. 2002-200054. In the host computer 6 of the case mentioned above, the untouched (i.e., automatically determined) candidate delay times $T_{DLa}$ and $T_{DLb}$ may automatically be set as the diagnostic imaging delay times $T_{DL1}$ and $T_{DL2}$. Alternatively, the automatically determined candidate delay times $T_{DLa}$ and $T_{DLb}$ may be presented to an operator as a candidate for the delay times $T_{DL1}$ and $T_{DL2}$, whereby the delay times $T_{DLa}$ and $T_{DLb}$ (e.g., as displayed reference information to the operator) may be set as the delay times $T_{DL1}$ and $T_{DL2}$ under the modification and approval of an operator.

Accordingly, the operator does not always need to determine the diagnostic imaging delay times $T_{DL1}$ and $T_{DL2}$, and thus the burden imposed on the operator can be reduced. Additionally, the substituted value of the delay times $T_{DL1}$ and $T_{DL2}$ can be automatically obtained on the basis of characteristics of the ECG-prep image, and thus it is possible to determine the value of proper delay times $T_{DL1}$ and $T_{DL2}$ in contrast with the case where an operator necessarily determines the value.

When the operator can identify blood flow parts in the ECG-prep image, delay times $T_{DL1}$ and $T_{DL2}$ that are more suitable for the delay times $T_{DL1}$ and $T_{DL2}$ can be determined by setting ROIs on the parts. However, when the operator does not need to set the ROI, the burden of the operator can be reduced.

Second Embodiment

The configurations of the MRI system according to a second embodiment are the same as those of the MRI system 100.

The second embodiment and the first embodiment are different in view of a process in the host computer 6 in order to determine the delay times $T_{DL1}$ and $T_{DL2}$.

Accordingly, hereinafter, the process in the host computer 6 according to the second embodiment for determining the delay times $T_{DL1}$ and $T_{DL2}$ will be described in detail.

Figure 6:
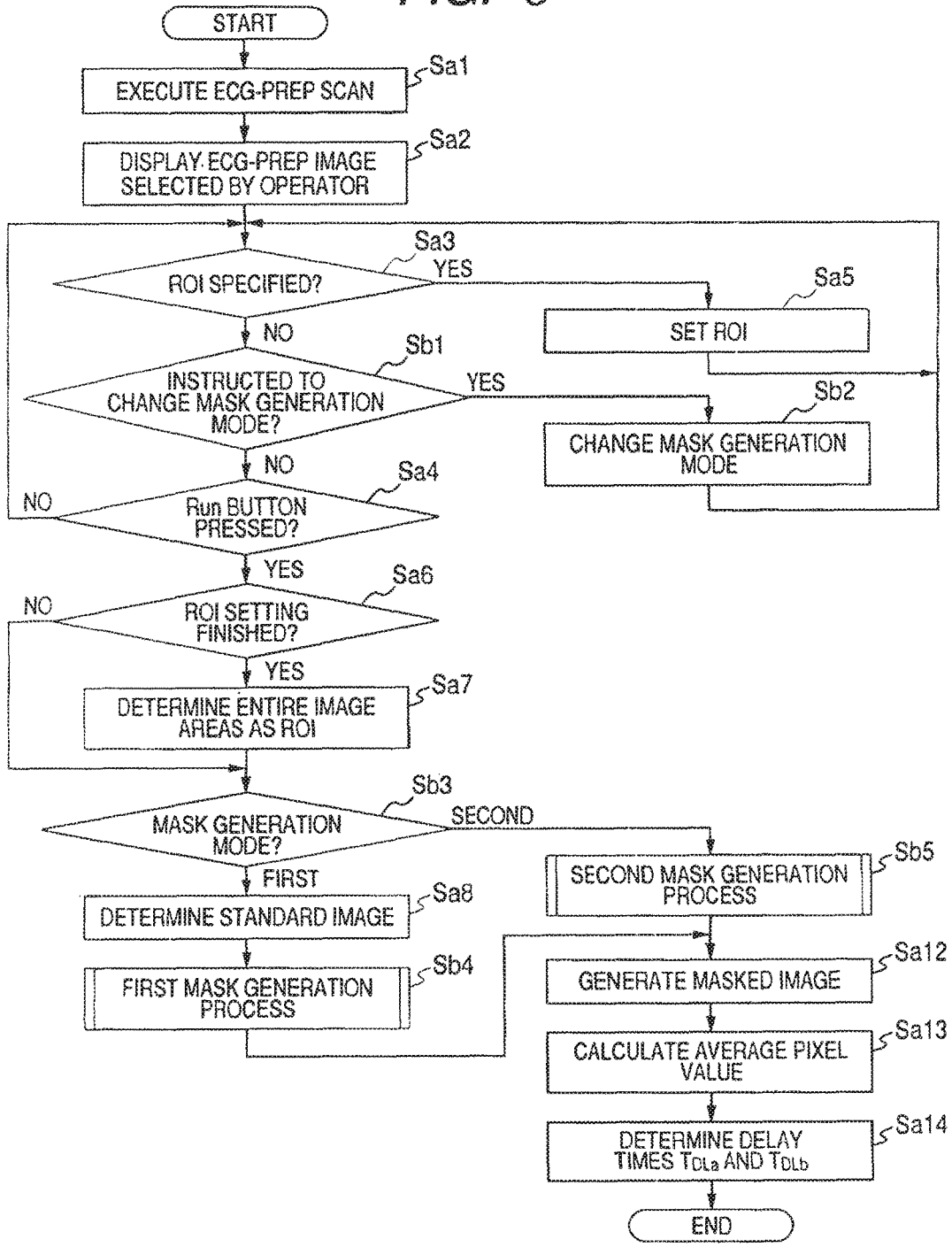
FIG. 6 is a flowchart illustrating the procedures of the host computer 6 for determining two delay times TDL1 and TDL2 according to a second embodiment.

FIG. 6 is a flowchart illustrating the procedures of the host computer 6 for determining two delay times 10 $T_{DL1}$ and $T_{DL2}$. The same step as FIG. 2 will be referenced by the same reference numerals and detailed description thereof will be omitted.

The host computer 6 becomes a waiting state after processing the steps Sa1 and Sa2 in the same manner as the first embodiment. In this waiting state, the host computer 6 performs a confirming in the step Sb1 in addition to the confirming in the steps Sa3 and Sa4.

Figure 7:
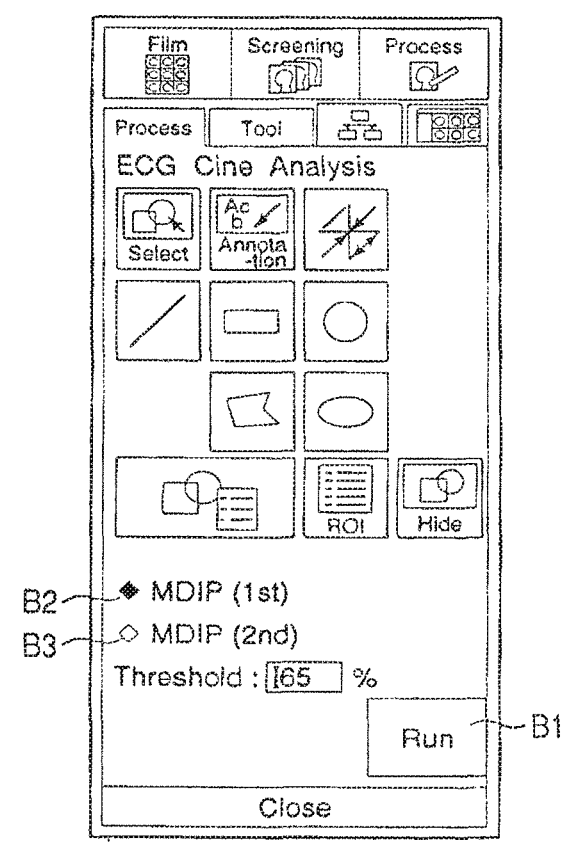
FIG. 7 is a diagram illustrating an example of a GUI displayed with the ECG-prep images in accordance with the second embodiment.

In this step Sb1, the host computer 6 confirms whether a command for changing the mask generation mode is given or not. To perform the command for changing the mask generation mode, in the host computer 6 according to the second embodiment, the GUI displayed to match the ECG-prep image with a screen in the step Sa2 is configured as the same configuration illustrated in FIG. 7. Option buttons B2 and B3 are disposed on the GUI illustrated in FIG. 7. The option buttons B2 and B3 is, one is a selection state, and the other one is a selection released state. The option buttons B2 and B3 correspond to the first and second modes, respectively.

When one of the option buttons B2 and B3 in the selection released state is clicked, the host computer 6 judges that a change of the mask generation mode is commanded, and the operations proceeds from the step Sb1 to the step Sb2. In the step Sb2, the host computer 6 changes the mask generation mode so as to be effective of the mode corresponding to the clicked option button. Thereafter, the host computer 6 returns to the waiting state of the steps Sa3, Sa4, and Sb1.

When the Run button B1 is pressed, the host computer 6 performs the operation of the step Sb3 after performing the steps Sa6 and Sa7 in a manner similar to the first embodiment. In the step Sb3, the host computer 6 confirms that the mask generation mode corresponds to which mode of the first mode or the second mode.

When the mask generation mode is in the first mode, the host computer 6 performs the operation of the step Sb8 after the step Sb3. Additionally, in the step Sa8, the host computer 6 determines the standard image in the same manner as the first embodiment, and then, in the step Sb4, executes the first mask generating process.

Figure 8:
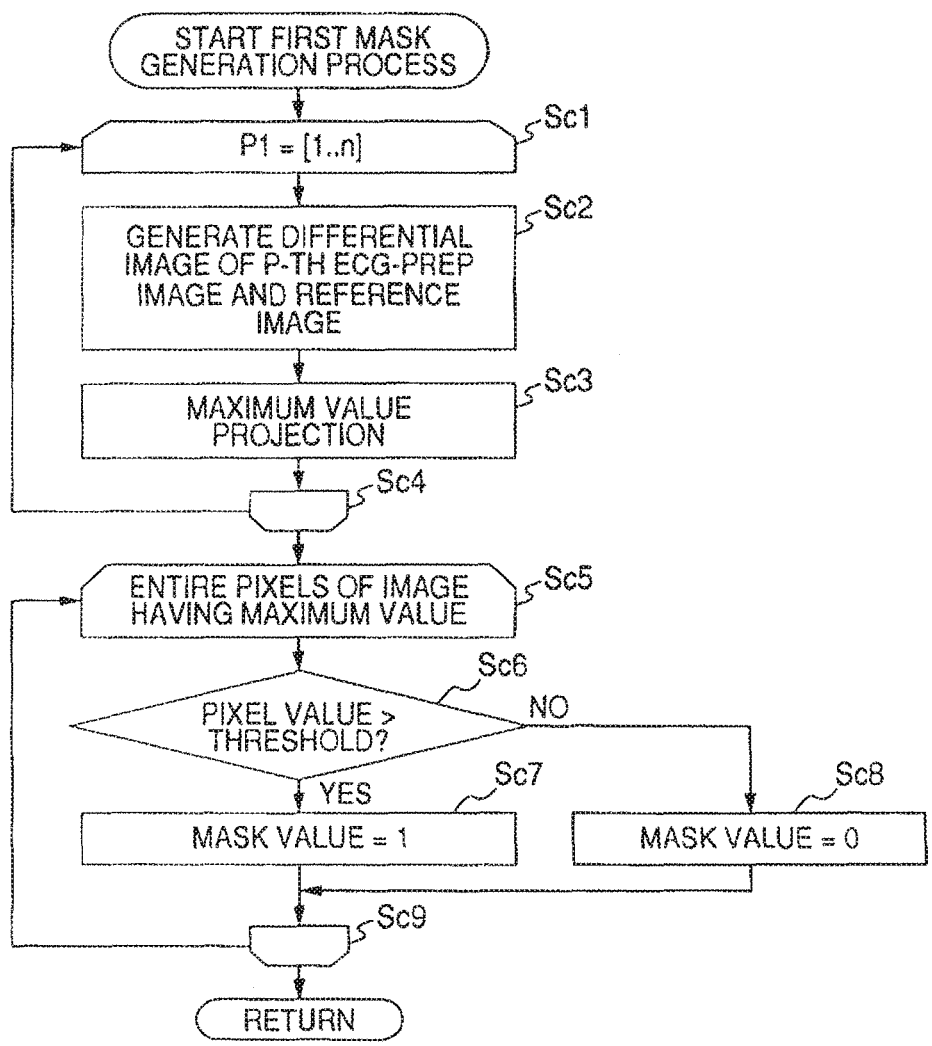
FIG. 8 is a flowchart illustrating the procedures of the host computer 6 for performing a first mask generating operation shown in FIG. 7.

FIG. 8 is a flowchart illustrating a first mask generating procedure performed by the host computer 6.

In the processing loop of the steps Sc1 to Sc4, the host computer 6 repeats the process of the steps Sc2 and Sc3 while increasing a variable P from "1" to "n," one by one. "n" is defined as the number of the ECG-prep image capable of being obtained in the step Sa1.

In the step Sc2, the host computer 6 generates a differential image between a P-th ECG-prep image and the standard image determined in the step Sa9. Next, in the step Sc3, the host computer 6 performs the maximum-value projection process on the maximum-value image previously generated in this first mask generating process and the differential image generated in the step Sc2, thereby generating one maximum-value image. When the variable P is "1," the first maximum-value projection is executed in this first mask generating process, the maximum-value image is not generated yet, and thus the differential image between the first ECG-prep image and the standard image just becomes the maximum-value image.

With such a configuration, when the processing loop of the step Sc1 to Sc4 is finished, one maximum-value image can be obtained. Consequently, the process in the processing loop of the step Sc1 to Sc4 is different in view of a detail procedure, but can obtain the same result as the process of the steps Sa9 and Sa10 according to the first embodiment.

Thereafter, in the processing loop of the steps Sc5 to Sc9, the host computer 6 repeats the process of the steps Sc6 to Sc8, while sequentially performing the process on the respective entire pixels of the maximum-value image.

In the step Sc6, the host computer 6 confirms whether the pixel value of the pixel subjected to the process is greater than the threshold or not. The threshold used in this step is the same as the threshold used in the step Sa11 according to the first embodiment. In addition, when the host computer 6 judges that the pixel value is greater than the threshold, the operation proceeds from the step Sc6 to the step Sc7, in which the host computer 6 sets a mask value corresponding to the pixel subjected to the process to "1." As compared therewith, when the host computer 6 judges that the pixel value is the threshold or less, the operation proceeds from the step Sc6 to the step Sc8, and a mask value corresponding to the pixel subjected to the process is set to "0."

With such a configuration, when the processing loop of the steps Sc5 to Sc9 is finished, a mask image in which the entire pixels of the maximum-value image are converted into binary values by the threshold can be obtained. Consequently, the process in the processing loop of the step Sc5 to Sc9 is different in view of a detail procedure, but can obtain the same result as the process of the step Sa11 according to the first embodiment.

Meanwhile, when the mask generation mode is in the second mode, the host computer 6 performs the step Sb5 after the step Sb3 in FIG. 6. Additionally, in the step Sb5, the host computer 6 executes a second mask generating process.

Figure 9:
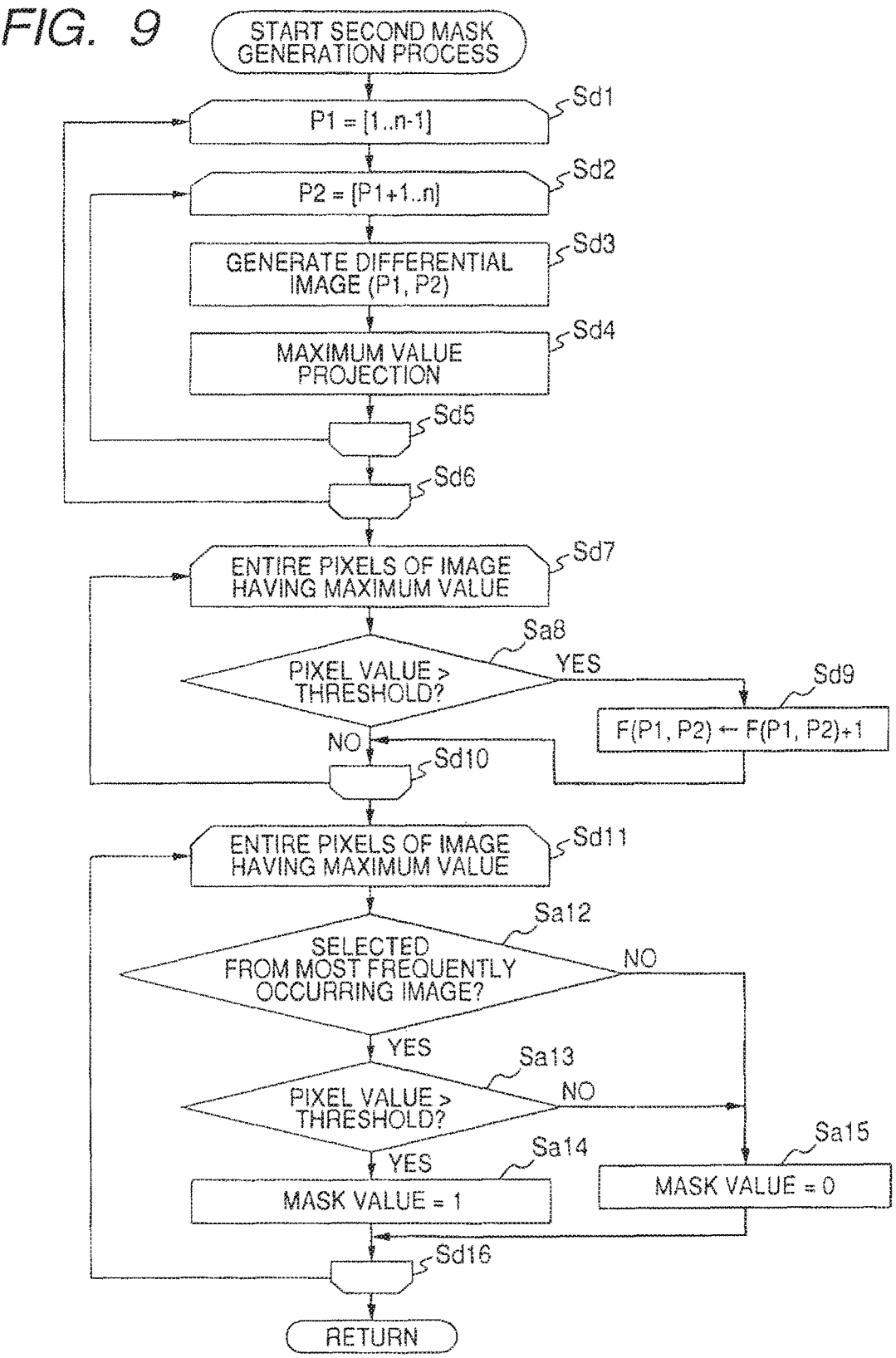
FIG. 9 is a flowchart illustrating the procedures of the host computer for performing a second mask generating operation shown in FIG. 7.

FIG. 9 is a flowchart illustrating the procedures of the host computer 6 in the second mask generating process.

In the processing loop of the steps Sd1 to Sd6, the host computer 6 repeats the process of the steps Sd2 to Sd5 while incrementing the variable P1 from "1" to "n−1," one by one.

In the processing loop of the steps Sd2 to Sd5, the host computer 6 repeats the process of the steps Sd3 and Sd4 while increasing a variable P2 from "P1+1" to "n," one by one.

In the step Sd3, the host computer 6 generates a differential image between a P1-th ECG-prep image and a P2-th ECG-prep image. Next, in the step Sd4, the host computer 6 performs the maximum-value projection process on the maximum-value image previously generated in this second mask generating process and the differential image generated in the step Sd3, thereby generating one maximum-value image. When the variable P1 is "1," the first maximum-value projection is executed in this second mask generating process, the maximum-value image is not generated yet, and thus the differential image between the first ECG-prep image and the second ECG-prep image just becomes the maximum-value image. The host computer 6 memorizes the differential images corresponding to the pixel values selected in the maximum-value projection process performed on each pixel of the maximum-value image.

With such a configuration, when the processing loop of the step Sd1 to Sd6 is finished, one maximum-value image can be obtained. The maximum-value image is obtained by executing the maximum-value projection process upon all differential images which are generated by all combinations (size nC2) of selecting the two images from the n ECG-prep images, respectively.

Thereafter, in the processing loop of the steps Sd7 to Sd10, the host computer 6 repeats the process of the steps Sd8 and Sd9, while sequentially performing the process on the respective entire pixels of the maximum-value image.

In the step Sd8, the host computer 6 confirms whether the pixel value of the pixel subjected to the process is greater than the threshold or not. The threshold used in this step is the same as the threshold used in the step Sa11 according to the first embodiment. When it is judged that the pixel value is greater than the threshold, the operation proceeds from the step Sd8 to the step Sd9, and the host computer 6 increments one frequency value F (P1, P2) of the differential images corresponding to the pixel values of the pixels subjected to the process. Specifically, for example, when the pixel value of the pixel subjected to the process is selected from the differential image between the 3rd and 8th ECG-prep images, a frequency value F (3, 8) increases one. An initial value of the frequency value F (P1, P2) is set to a common value such as "0." As compared therewith, when the host computer 6 judges that the pixel value is the threshold or less, the operation proceeds from the step Sd8 to the step Sd10, and the frequency value F (P1, P2) is not entirely changed.

When the processing loop of the steps Sd7 to Sd10 is finished, the frequency value F (P1, P2) indicative of a frequency of selecting the pixel from the current differential image among the plurality of differential images in the maximum value control process.

Next, in the processing loop of the steps Sd11 to Sd16, the host computer 6 repeats the process of the steps Sd12 to Sd15 while sequentially executing the respective entire pixels of the maximum-value image. In the steps Sd12 and Sd13, the host computer 6 confirms whether the pixel value of the pixel subjected to the process is selected from the maximum-frequency image and greater than the threshold or not. The maximum-frequency image used in this step is a differential image of which the frequency value F (P1, P2)

is the largest value. Additionally, the threshold is the same as the threshold used in the step Sd8.

When it is judged that the aforementioned condition is satisfied, the operation proceeds from the step Sd13 to the step Sd14, in which the host computer 6 sets a mask value corresponding to the pixel 10 subjected to the process to "1." On the other hand, when it is judged that the aforementioned condition is not satisfied, the operation proceeds from the steps Sd12 or Sd13 to the step Sd15, in which the host computer 6 sets a mask value corresponding to the pixel subjected to the process to "0."

When the processing loop of the steps Sd11 to Sd16 is finished, a mask image converted into binary values can be obtained in which only the mask values corresponding to the pixel selected from the maximum-frequency image and having a pixel value larger than the threshold are set to "1" and the mask values corresponding to the other pixels are set to "0."

After finishing the first mask generating process or the second mask generating process described above, the host computer 6 executes the steps Sa12 to Sa14 in the same manner as the first embodiment.

With such a configuration, the delay times $T_{DLa}$ and $T_{DLb}$ are practically determined in the same manner as the first embodiment, when the mask generation mode is in the first mode. However, the mask image is generated on the basis of the maximum-value image obtained by generating differential images with respect to respective all combinations of $n^2$ which is the number of cases capable of selecting two images from n ECG-prep images, and by executing a maximum-value projection process upon the plurality of generated differential images, when the mask generation mode is in the second mode. For this reason, the mask image can be generated in consideration of the case where the larger signal variation occurs between the ECG-prep images other than the ECG-prep image of the standard image in the first embodiment. In the first embodiment, precision of the mask image can be easy to vary, since pixel value intensity of the maximum-value image varies with a time phase belonging to the ECG-prep image which is selected as a standard image. However, in the manner of second mode according to the second embodiment, the large signal variation as described above can be surely reflected on the pixel value of the maximum-value image, and the mask image having a good precision can be stably generated.

Occasionally, the intensity of the signal is greatly fluctuated by some influences such as intestinal peristalsis other than the blood vessel. In the second mode, such a signal variation is occasionally reflected on the pixel value of the maximum-value image. However, since the intestinal peristalsis has no relation with heart motion, such a pixel value has a low possibility to be selected as a differential image between an ECG-prep image based on the time phase in the vicinity of a systolic period and an ECG-prep image based on a time phase in the vicinity of a diastolic period. Meanwhile, the difference between signals from the blood vessel mostly becomes the maximum between the systolic period and the diastolic period. For this reason, a pixel value representing large variation in the signal intensity from the blood vessel has a high possibility to be selected as a differential image between an ECG-prep image based on the time phase in the vicinity of a systolic period and an ECG-prep image based on a time phase in the vicinity of a diastolic period, and these pixel values mostly belong to the maximum-value image. In the second mode, though a pixel value is greater than a threshold, if the pixel value is not selected from the maximum-frequency image, a mask value is set to "0." As a result, it is possible to generate a high precision mask image without influence of intestinal peristalsis and the like.

Figure 10:
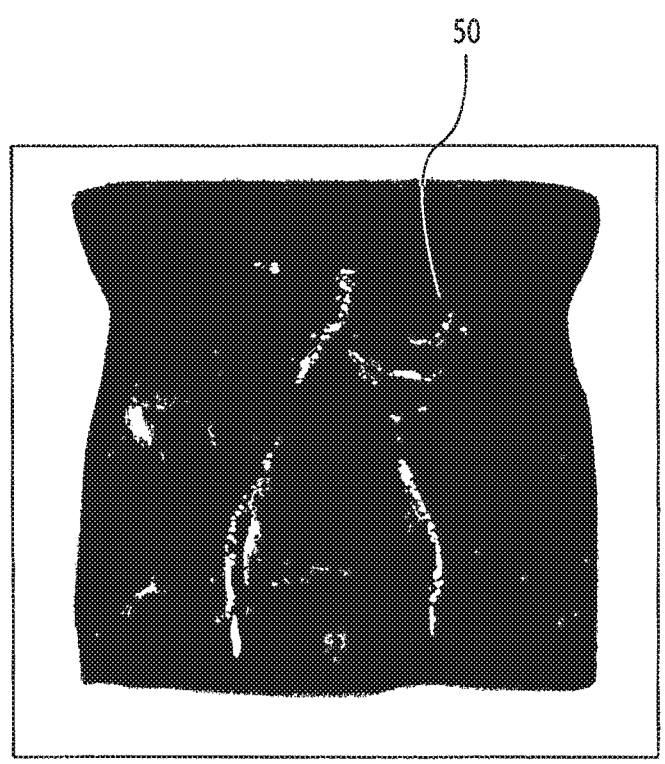
FIG. 10 is a diagram illustrating an example of a mask image.

FIG. 10 is a diagram illustrating an example of a mask image. FIG. 10 represents the pixel of which a mask value in a mask image is "1" in white color. The maximum-value image is represented as a background image of the mask image by applying the pixel value in the maximum-value image to the pixel of which a mask value in a mask image is "0." When the pixel value in the maximum-value image is threshold or more but the pixel value is not selected from the maximum-frequency image, the pixel of which a mask value in a mask image is "0" is represented as reducing brightness thereof. Accordingly, for example, the uneven part denoted as the reference numeral 50 corresponds to the region in which signal intensity has been greatly varied by influences such as intestinal peristalsis.

Third Embodiment

The outlined configuration of the MRI system according to a third embodiment is the same as the MRI system 100.

The third embodiment and the first embodiment are different in that the host computer 6 has an additional function of generating a reference image for determining a position to be described later on the basis of an ECG-prep image in addition to the various kinds of control functions executed by software procedures memorized.

Hereinafter, an operation of the case of performing an imaging in the Flow-Spoiled FBI method will be described in the third embodiment. An operation of the case of performing an imaging to obtain a coronal image in the Flow-Spoiled FBI method upon the legs of the subject 200 will be described in this section.

Figure 11:
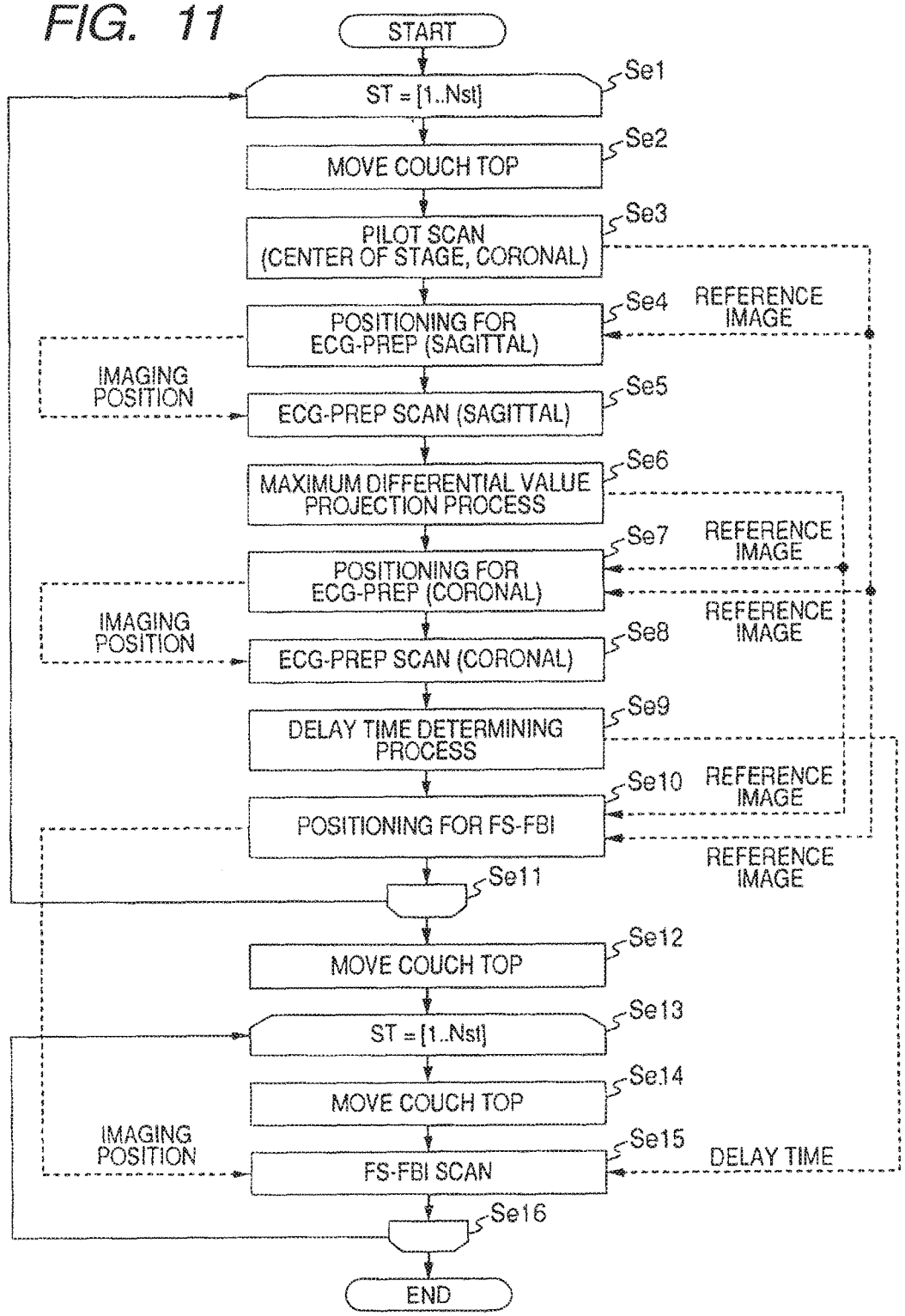
FIG. 11 is a flowchart illustrating the procedures of the host computer when an imaging process is performed using a Flow-Spoiled FBI method according to a third embodiment.

FIG. 11 is a flowchart illustrating a procedure performed by a host computer 6 when an imaging process is performed by a Flow-Spoiled FBI method.

In the processing loop of the steps Se1 to Se11, the host computer 6 repeats the process of the steps Se2 to Se10 while increasing a variable ST from "1" to "Nst," one by one. "Nst" is defined as the number of divisions in case where the region subjected to the MR scan of the Flow Spoiled FBI method is divided plural times, that is so-called stage number.

In the step Se2, the host computer 6 causes the couch top to move so as to move the subject 200 to the position suitable for imaging a ST-th stage.

In the step Se3, the host computer 6 instructs the sequencer 5 to execute a pilot scan upon a coronal surface with respect to the center of stage. The sequencer 5 executes the pilot scan to obtain the pilot image in the known procedure in accordance with the instruction.

In the step Se4, the host computer 6 executes a positioning for ECG-prep scan upon the sagittal surface, by using the aforementioned pilot image employed as a reference image. This positioning may be automatically performed by the host computer 6, and may be performed by inputting information of the position specified by an operator. In the case of the latter, the pilot image is presented to an operator in such a manner of displaying the image employed as the reference image on the display unit 12.

In the step Se5, the host computer 6 instructs the sequencer 5 so as to execute the ECG-prep scan upon the sagittal surface positioned in the step Se4. Then, according to the instruction, the sequencer 5 executes the ECG-prep scan upon the specified sagittal surface in the procedure disclosed in Japanese Unexamined Patent Application Publication No. 2002-200054.

In the step Se6, the host computer 6 executes a maximum differential intensity projection process (MDIP process) upon the plurality of ECG-prep images acquired in the step Se5. As for the maximum differential intensity projection process, it can be applied that one of the processes such as the processes of the steps Sa8 to Sa11 in FIG. 2, the processes of the steps Sa8 and Sb4 in FIG. 6, and the process of the step Sb5. Consequently, the host computer 6 generates the mask image generated in the same manner in the first or second embodiment on the basis of the plurality of ECG-prep images acquired from the step Se5, in this step Se6.

In the step Se7, the host computer 6 executes a positioning for ECG-prep scan upon the coronal surface, by using the aforementioned pilot image and mask image generated in the step Se3 so as to be used as reference images, respectively. Since the aforementioned mask image is an image in which features of blood vessels are extracted as described in the first embodiment and the second embodiment, it is able to easily perform a positioning suitable for imaging the blood vessels by using the mask image employed as a reference image. Moreover, since the aforementioned mask image is a sagittal image, the legs of subject can be suitably depicted when the subject stretches his legs in a straight shape. Accordingly, the aforementioned mask image is used as a reference image, and thus it is possible to easily perform the positioning suitable for imaging bent legs. This positioning may be automatically performed by the host computer 6, and may be performed by inputting information of the position specified by an operator. In the case of the latter, the pilot image is presented to an operator in such a manner of displaying the image employed as the reference image on the display unit 12.

In the step Se8, the host computer 6 instructs the sequencer 5 so as to execute the ECG-prep scan upon the coronal surface positioned in the step Se7. Then, according to the instruction, the sequencer 5 executes the ECG-prep scan upon the specified coronal surface in the procedure disclosed in Japanese Unexamined Patent Application Publication No. 2002-200054.

In the step Se9, the host computer 6 executes a delay time determining process upon a plurality of ECG-prep images acquired in the step Se8. As for the longest delay time determining process, for example, processes of the steps Sa2 to Sa14 in FIG. 2 can be applied. In the step Se9, the host computer 6 determines the delay times $T_{DLa}$ and $T_{DLb}$ as a substitution for the delay times $T_{DL1}$ and $T_{DL2}$ in the MR scan (hereinafter, it is referred to as a FS-FBI scan) of the Flow-Spoiled FBI method disclosed in the Japanese Unexamined Patent Application Publication No. 2002-200054, on the basis of the plurality of ECG-prep images acquired in the step Se8. In the host computer 6, the untouched delay times $T_{DLa}$ and $T_{DLb}$ may automatically be set as the delay times $T_{DL1}$ and $T_{DL2}$, but the delay times $T_{DLa}$ and $T_{DLb}$ are also presented (e.g., to an operator) as a proposed substitution (e.g., reference information) for the delay times $T_{DL1}$ and $T_{DL2}$, whereby the delay times $T_{DLa}$ and $T_{DLb}$ may be set as the delay times $T_{DL1}$ and $T_{DL2}$ under the modification and approval of an operator.

In the step Se10, the host computer 6 executes a positioning upon 3-dimensional region subjected to the FS-FBI scan, by using the aforementioned pilot image generated in the step Se3 and mask image generated in the step Se6 so as to be used as reference images, respectively. In this positioning, it is able to easily and properly perform the positioning in the same manner of the step Se7 by using the mask image employed as a reference image. This positioning may be automatically performed by the host computer 6, and may be performed by inputting information of the position specified by an operator. In the case of the latter, the pilot image is presented to an operator in such a manner of displaying the mask image generated in the step Se6 as the reference image on the display unit 12. Instead of the pilot image, the mask image generated in the step Se9 can be used as a reference image.

With such a configuration, when the processing loop of the steps Se1 to Se11 is finished, the positioning for the FS-FBI scan with respect to the Nst stage is finished.

In the step Se12, the host computer 6 causes the couch top to move so as to return the subject 200 to the standard position.

Thereafter, the host computer 6 executes the processing loop of the steps Se1 to Se11. In the processing loop of the steps Se1 to Se11, the host computer 6 repeats the process of the steps Se14 and Se15 while increasing a variable ST from "1" to "Nst," one by one.

In the step Se14, the host computer 6 causes the couch top to move so as to move the subject 200 to the position suitable for imaging a ST-th stage.

In the step Se15, the host computer 6 instructs the sequencer 5 to execute the FS-FBI scan upon a coronal surface of the position determined with respect to the ST-th stage in the step Se10. At that time, the host computer 6 notifies the sequencer 5 of the delay times TDL1 and TDL2 determined with respect to the ST-th stage in the step Se9. The sequencer 5 executes the FS-FBI scan for the specified 3-dimensional region, for example, in the procedure disclosed in Japanese Unexamined Patent Application Publication No. 2002-200054, in accordance with the instruction.

With such a configuration, when the processing loop of the steps Se13 to Se16 is finished, the FS-FBI scan with respect to the Nst stage is finished.

According to the third embodiment, it is possible to properly and easily perform the positioning based on running of blood flow as mentioned above, since the mask image generated by the maximum differential intensity projection process is used as a reference image for positioning of ECG-prep scan and FS-FBI scan upon the coronal surface.

The embodiments may be modified to various forms as follows.

Figure 12:
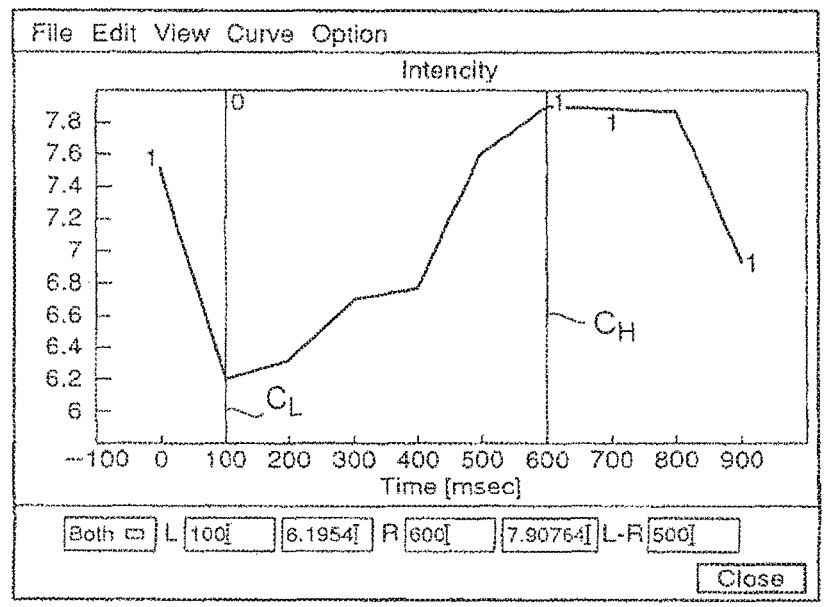
FIG. 12 is a diagram illustrating an example of an image in which the average pixel value is depicted so as to correspond to the delay time of the time phase thereof.
Figure 13:
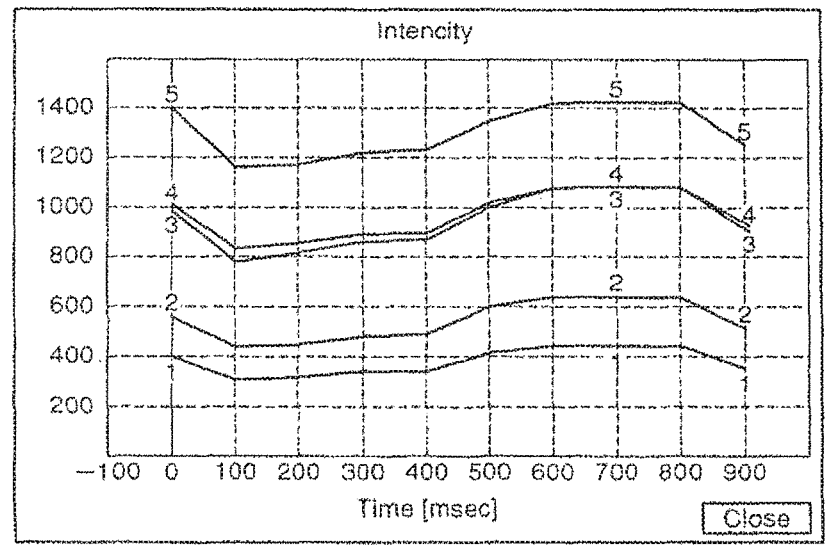
FIG. 13 is a diagram illustrating another example of an image, in which the average pixel value is depicted so as to correspond to the delay time of the time phase thereof.

(1) The determination of the delay times $T_{DLa}$ and $T_{DLb}$ may not be performed in the system, but rather the determining may be performed by an operator. In this case, generating the reference information as a graphical image which is represented by making the average pixel value (ordinate) calculated in the step Sa13 correspond to the delay time of the time phase (abscissa). As illustrated in FIGS. 12 and 13, for example, the graphical image is presented to an operator as additional reference information by displaying the graphical image on the display unit 12. With such a configuration, the operator can determine the delay times $T_{DLa}$ and $T_{DLb}$ by simply comparing between numerical values. This method is very simple in comparison with subjectively determining the delay times $T_{DLa}$ and $T_{DLb}$ on the basis of only the ECG-prep images. FIG. 12 is an example in the case of just one ROI, and FIG. 13 is an example in the case of five ROIs.

Compared with the case where the delay times TDLa and TDLb determined by an operator are inputted as the numerical values, the burden imposed on the operator can be reduced when cursors CL and CH are displayed as illustrated in FIG. 12, the cursors CL and CH are shifted in a time direction in accordance with instructions of the operator, the delay time corresponding to a position of the cursor CL is set to delay time $T_{DLa}$, and the delay time corresponding to a position of the cursor CL is set to delay time $T_{DLb}$.

The image presented to the operator may have an expression form, such as a table form, that is different from those shown in FIGS. 12 and 13.

The automatic determination result may be confirmed by an operator in such a manner that the display unit 12 displays the image as shown in FIG. 12 in which the cursors CL and CH are shifted so as to correspond to the automatically determined delay times $T_{DLa}$ and $T_{DLb}$ in a manner similar to the aforementioned embodiment. In this case, the cursors CL and CH may be shifted in a time direction in accordance with instructions of the operator, and the delay times $T_{DLa}$ and $T_{DLb}$ may be manually adjusted. When the display unit 12 displays the differential image between the ECG-prep image and the standard image corresponding to the positions of the cursors CL and CH, the operator can confirm whether the current time phase is suitable for the determination of the delay times $T_{DLa}$ and $T_{DLb}$.

Figure 14:
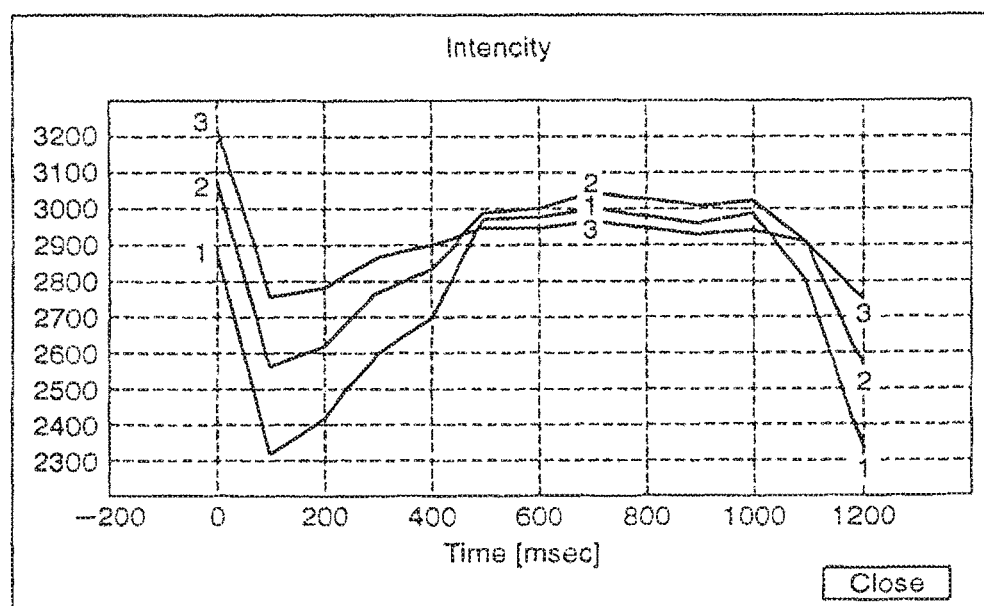
FIG. 14 is a diagram illustrating an example of an image for depicting the temporal variations of a plurality of average values obtained by using a plurality of thresholds.

(2) The step Sa11 may be configured to generate a plurality of mask images using a plurality of mutually different thresholds, and the steps Sa12 and Sa13 may be configured to perform corresponding operations on the basis of the plurality of mask images, so that a plurality of average values can be obtained for one time phase. In this case, the process of the step Sa14 is not performed, and the image as illustrated in FIG. 8 is presented to an operator, in which the aforementioned average values are depicted as temporal variation for each threshold. In FIG. 14, the curve 1 corresponds to the case of setting a threshold to "0.8"; the curve 2 corresponds to the case of setting a threshold to "0.5"; and the curve 3 corresponds to the case of setting a threshold to "0.2."

As shown in FIG. 14, the time phases corresponding to the maximum and minimum average values do not change greatly with the change in the thresholds, but the difference between the maximum average value and the minimum average value decrease with the decrease in the threshold. When a larger threshold is used, it is likely to find the parts having a large variation in flow rate, that is, the parts having a high possibility of being the blood flow. However, when a smaller threshold is used, it is likely to erroneously extract parts other than the blood vessels and thus deteriorate reliability of the result. On the other hand, the smaller threshold is useful for acquiring a wide range of information about the blood vessels.

For this reason, by presenting the image as illustrated in FIG. 14 to an operator, it is possible to provide more information to the operator for judgment ground. For example, if there are a case where a time phase A is extracted as the maximum signal time phase (diastolic period) using a larger threshold and a case where a time phase B is extracted as the maximum signal time phase (diastolic period) using a smaller threshold, the operator can select better one based on the difference between the extraction results by comparing the images obtained from the time phase A and the time phase B.

(3) The invention may be applied not only to the Flow-Spoiled FBI method but also to FBI method and other methods such as the ECG-gating imaging method.

(4) Instead of the ECG signal, a pulse wave signal may be used. For example, the MR scan may be performed in synchronization with the pulse wave signal which can be obtained by a sphygmograph attached to the finger edge of a subject. It is difficult to detect a systolic period on the basis of the pulse wave signal compared with the case of detecting the systolic period on the basis of the electrocardio signal. However, in the embodiments of the present application, even when the pulse wave signal is used instead of the ECG signal, it is possible to generate the image in which feature of blood vessels is properly extracted. Accordingly, the positioning or determination of the delay time can be properly performed. In this case, since the blood flow change from the maximum to the minimum and the pulse wave changes from the minimum to the maximum, a synchronous imaging is performed in consideration of this feature. The image of the initial time phase of both electrocardio signal and pulse wave signal is occasionally shaken, and thus the image may be configured to be removed from analysis.

Figure 15:
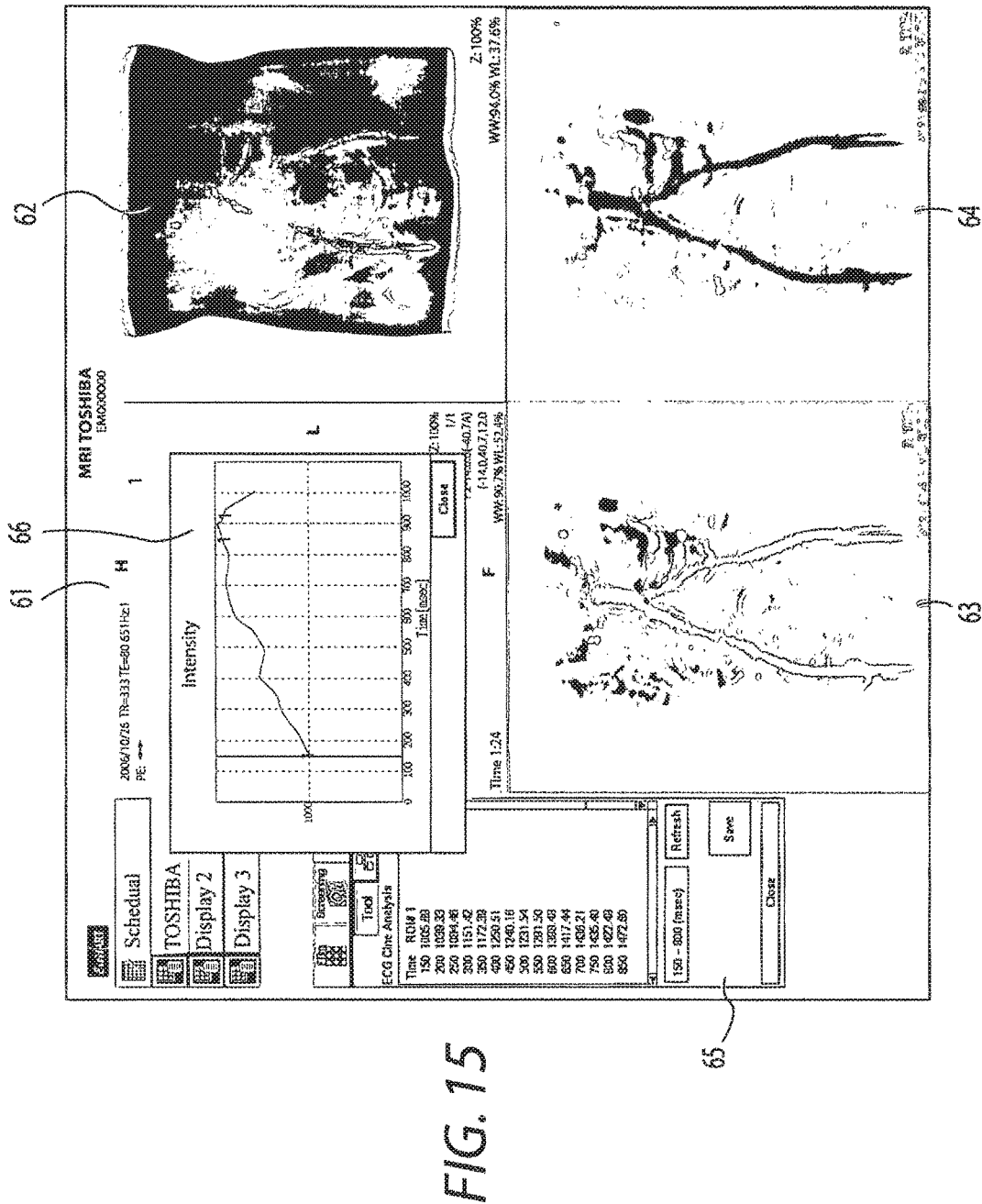
FIG. 15 is a diagram illustrating an example of a screen for displaying a processing result.

(5) A processing result may be displayed on a screen as illustrated in FIG. 15 by the display unit 12, for example. On the screen illustrated in FIG. 15, the images 61 to 64 and a GUI 65 are arranged with the image 66 superimposed thereon. The image 61 is of the same kinds as the image illustrated in FIG. 4 or FIG. 5, and is used for setting the ROI. The image 62 is of the same kinds as the image illustrated in FIG. 10, and represents the mask image. The images 63 and 64 represent a differential image of two time phases that are selected by the use of the GUI 65. When the images of the two time phases selected by the use of the GUI 65 are set to the first image and the second image, the differential image obtained by subtracting the second image from the first image corresponds to the image 63, and the differential image obtained by subtracting the first image from the second image corresponds to the image 64. The image 66 is of the same kinds as the image illustrated in FIG. 12 or FIG. 13, and is a graph used for judging the optimum time phase.

(6) In the second embodiment, the steps Sb3, Sa8, and Sb4 may be omitted, and the second mask generating process may be performed in any cases.

(7) In the third embodiment, a slice plane of the pilot scan in the step Se3 or the ECG-prep scan in the steps Se5 and Se8 may vary with a slice plane of the FS-FBI scan. That is, the slice plane of the ECG-prep scan in the step Se8 may correspond to the slice plane of the FS-FBI scan. The slice plane of the ECG-prep scan in the step Se5 may be orthogonal to the slice plane of the FS-FBI scan. The slice plane of the pilot scan in the step Se3 may be orthogonal to the slice plane of the ECG-prep scan in the step Se5.

(8) In the third embodiment, the delay time determining process may be configured to receive specifications from an operator in a similar manner to the conventional one.

The invention is not limited to the embodiments described above, but may be embodied and modified in various forms without departing from the spirit of the invention in implementation steps. A plurality of components disclosed in the embodiments may be suitably combined with each other to produce various aspects of the invention. For example, several components may be removed from the entire components disclosed in the embodiments. The components of one embodiment may be properly combined with components of the other embodiments.

Additional advantages and modifications will readily occur to those skilled in the art. Therefore, the invention in its broader aspects is not limited to the specific details and representative embodiments shown and described herein. Accordingly, various modifications maybe made without

What is claimed is:

1. A magnetic resonance imaging system comprising:
a prep scan section configured to perform a prep scan acquiring plural sets of echo signals at a plurality of cardiac time phases corresponding to time delays in a cardiac cycle, wherein each of the plurality of cardiac time phases are mutually different from each other for each slice position of the prep scan;
a reference information acquiring section configured to acquire reference information representing a functional relationship between the time delays and pixel values based on the plurality of prep images for use in determining a first cardiac time phase and a second cardiac time phase, the functional relationship being graphable;
a reference information display section configured to display said reference information as a graph of the pixel values versus the time delays which represents the functional relationship;
a prep image generating section configured to generate a plurality of prep images respectively corresponding to the plurality of cardiac time phases on the basis of the plural sets of echo signals;
a cardiac time phase determining section configured to automatically determine a first cardiac time phase and a second cardiac time phase on the basis of the functional relationship between the time delays corresponding to cardiac time phases and pixel values derived from the plurality of prep images;
a diagnostic imaging scan section configured to acquire diagnostic imaging echo signals by performing a diagnostic imaging scan upon each of the first cardiac time phase and the second cardiac time phase which are automatically set by the cardiac time phase determining section; and
imaging diagnostic image generating section configured to generate a first image based on an echo signal of the first cardiac time phase obtained by the diagnostic imaging scan section, to generate a second image based on an echo signal of the second cardiac time phase obtained by the diagnostic imaging scan section, and to acquire a differential diagnostic image by calculating a difference between the first image and the second image.

2. The magnetic resonance imaging system according to claim 1, wherein the cardiac time phase determining section generates a mask image on the basis of the plurality of prep images and calculates a feature quantity of the plurality of cardiac time phase on the basis of the mask image and the plurality of prep images.

3. The magnetic resonance imaging system according to claim 2, wherein the mask image is a maximum-value image obtained by performing a maximum-value projection process on the plurality of prep images or a plurality of differential images obtained by calculating a difference between the plurality of prep images and a standard image which is one of the plurality of prep images.

4. The magnetic resonance imaging system according to claim 3, wherein the mask image is a binarized image obtained by binarizing the maximum-value image.

5. The magnetic resonance imaging system according to claim 4, further comprising:

a masked image generating section configured to generate a plurality of masked images by masking images of the ROIs in the plurality of prep images by the use of the binarized image; and
an average calculating section configured to calculate an average intensity to be used as the feature quantity of respective pixels in each masked image as the feature quantity.

6. The magnetic resonance imaging system according to claim 4, further comprising:
a maximum-frequency image determining section configured to determine which of the plurality of prep images is the maximum-frequency image from which the largest number of intensities are selected in the maximum-value projection process; and
a replacing section configured to generate the binarized image by replacing the intensity selected from the maximum-frequency image and greater than a threshold with a first value and replacing the other pixel values with a second value different from the first value.

7. The magnetic resonance imaging system according to claim 2, wherein the cardiac time phase determining section generates the mask image on the basis of partial data of the respective prep images.

8. The magnetic resonance imaging system according to claim 7, the system further comprises an ROI (region of interest) setting section configured to set a part of the respective prep images to an ROI,
wherein the cardiac time phase determining section generates the mask image on the basis of data of the ROI.

9. The magnetic resonance imaging system according to claim 2, further comprising a cardiac time phase determining section configured to determine the first cardiac time phase and the second cardiac time phase on the basis of the feature quantity.

10. The magnetic resonance imaging system according to claim 2,
wherein the prep scan section acquires plural sets of echo signals of the respective plural cardiac time phases at each slice position in a section orthogonal to a section from which the diagnostic image should be acquired or a section of a final diagnostic image obtained by performing an image process, and
wherein the system further comprises a positioning section configured to display the mask image as a positioning image on which the diagnostic imaging scan is performed.

11. The magnetic resonance imaging system according to claim 10, further comprising:
a pilot scan section configured to perform a pilot scan of acquiring echo signals in a section parallel to a section from which the diagnostic image or a section of the final diagnostic image is obtained; and a
pilot image generating section configured to generate a pilot image, on the basis of the echo signals acquired by the pilot scan section, wherein the positioning section uses the pilot image as a reference image.

12. The magnetic resonance imaging system according to claim 2, wherein the mask image is a maximum-value image obtained by generating differential images in all combinations of two images selected from the plurality of prep images, and performing a maximum-value projection process upon the generated differential images.

13. The magnetic resonance imaging system according to claim 12, wherein the mask image is a binarized image obtained by binarizing the maximum-value image.

14. The magnetic resonance imaging system according to claim 13, further comprising:
- a mask image generating section configured to generate a plurality of mask images by masking images of the ROIs in the plurality of prep images by the use of the binarized image; and
- an average calculating section configured to calculate an average intensity of pixels in each mask image as the feature quantity.

15. The magnetic resonance imaging system according to claim 13, further comprising:
- a maximum-frequency image determining section configured to determine which of the plurality of prep images is the maximum-frequency image from which the largest number of intensities are selected in the maximum-value projection process; and
- a replacing section configured to generate the binarized image by replacing the intensity selected from the maximum-frequency image and greater than a threshold with a first value and replacing the other pixel values with a second value different from the first value.

16. The magnetic resonance imaging system according to claim 1, wherein the first cardiac time phase and the second cardiac time phase are in a systolic period and a diastolic period, respectively.

17. The magnetic resonance imaging system according to claim 1, wherein the prep scan section or the imaging scan section judges the cardiac time phases on the basis of a signal obtained by a sphygmograph.

18. The magnetic resonance imaging system according to claim 1, wherein the prep scan section acquires plural sets of echo signals corresponding to a plurality of cardiac time phases for each slice position in a plurality of sections orthogonal to each other, and
- wherein the cardiac time phase determining section generates a first mask image on the basis of the plurality of prep images in a first section of the plurality of sections orthogonal to each other, and generates a second mask image on the basis of the plurality of prep images in a second section.

19. The magnetic resonance imaging system according to claim 1, further comprising a movable section configured to move a subject to be examined by the diagnostic imaging scan,
- wherein the diagnostic imaging scan section performs the diagnostic imaging scan upon a plurality of stages at which the subject is moved or a plurality of photographing regions of the subject.

20. The magnetic resonance imaging system according to claim 1, wherein the prep scan section performs a plurality of prep scans at each slice position plural times by changing a delay time from a reference time phase of the cardiac time phases of a subject to be examined by the imaging scan to a start time of the prep scan.

21. A magnetic resonance imaging method comprising steps of:
- performing a prep scan acquiring plural sets of echo signals at a plurality of cardiac time phases corresponding to time delays in a cardiac cycle, wherein each of the plurality of cardiac time phases are mutually different from each other for each slice position of the prep scan;
- generating a plurality of prep images respectively corresponding to the plurality of cardiac time phases on the basis of the plural sets of echo signals;
- acquiring reference information representing a functional relationship between the time delays and pixel values based on the plurality of prep images for use in determining a first cardiac time phase and a second cardiac time phase, the functional relationship being graphable;
- displaying said reference information as a graph of the pixel values versus the time delays which represents the functional relationship;
- automatically determining a first cardiac time phase and a second cardiac time phase on the basis of the functional relationship between the time delays corresponding to cardiac time phases and pixel values derived from the plurality of prep images;
- acquiring diagnostic imaging echo signals by performing a diagnostic imaging scan upon each of the first cardiac time phase and the second cardiac time phase which are automatically set in the cardiac time phase determination; and
- generating a first image based on an echo signal of the first cardiac time phase obtained by the diagnostic imaging scan section, generating a second image based on an echo signal of the second cardiac time phase obtained by the diagnostic imaging scanning, and acquiring a differential diagnostic image by calculating a difference between the first image and the second image.

* * * * *